United States Patent
Viltro et al.

(10) Patent No.: US 6,648,641 B1
(45) Date of Patent: Nov. 18, 2003

(54) APPARATUS, METHOD AND PRODUCT FOR TREATING TEETH

(75) Inventors: Louis John Viltro, Hamilton, OH (US); Scott Matthew Wright, Cincinnati, OH (US); Patrick John Healey, West Chester, OH (US); Giovanni Battista de Amicis, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/721,431

(22) Filed: Nov. 22, 2000

(51) Int. Cl.⁷ .................. A43D 44/18; A61C 15/00
(52) U.S. Cl. .................. 433/80; 132/308; 433/216
(58) Field of Search ............ 433/80, 89, 216; 132/308; 401/45, 46, 47; 222/145.3, 145.4

(56) References Cited

U.S. PATENT DOCUMENTS

| | | | |
|---|---|---|---|
| 368,373 A | 8/1887 | Blinn | |
| 730,040 A | 6/1903 | McKinley et al. | |
| 904,190 A | 11/1908 | Fesler | |
| 1,007,042 A | * 10/1911 | Mosby | 401/45 |
| 1,060,524 A | 4/1913 | Wolfe | |
| 1,601,596 A | * 9/1926 | Paskach | 401/45 |
| 1,809,330 A | 6/1931 | Dorrance et al. | |
| 3,056,151 A | * 10/1962 | Vlacancich | 401/45 |
| 3,187,360 A | 6/1965 | Spohr | 15/22 |
| 3,217,720 A | 11/1965 | Cyzer | 132/84 |
| 3,619,074 A | * 11/1971 | Morawski | 401/45 |
| 3,907,441 A | 9/1975 | Idec et al. | 401/75 |
| 3,927,435 A | 12/1975 | Moret et al. | 16/176 |
| 4,013,370 A | 3/1977 | Gingras | 401/175 |
| 4,019,654 A | 4/1977 | van Manen | 222/1 |
| 4,046,288 A | 9/1977 | Bergman | 222/135 |
| 4,060,870 A | 12/1977 | Cannarella | |
| 4,071,300 A | 1/1978 | Nichols et al. | 401/175 |
| 4,139,114 A | 2/1979 | Long et al. | 220/23.4 |
| 4,434,810 A | 3/1984 | Atkinson | 137/493 |
| 4,693,622 A | 9/1987 | Booth | 401/191 |
| 4,895,276 A | 1/1990 | Maldonado | 221/144.5 |
| 4,948,737 A | 8/1990 | Quenin et al. | 436/46 |
| 5,058,230 A | 10/1991 | Hodosh et al. | 15/167.1 |
| 5,088,850 A | 2/1992 | Taichman et al. | |

(List continued on next page.)

FOREIGN PATENT DOCUMENTS

| | | |
|---|---|---|
| DE | 93 16 316.9 | 4/1994 |
| FR | 2 700 678 | 7/1994 |
| GB | 2 307 674 A | 6/1997 |

*Primary Examiner*—Todd E. Manahan
(74) *Attorney, Agent, or Firm*—Peter D. Meyer

(57) ABSTRACT

A brushing system including a multiple cartridge dispensing system which dispenses the treatment material either directly onto brush bristles, or through the brush to the bristles. A multiplicity of materials may be provided to the cartridges for use in brushing. In addition to use in dental care, the system finds utility in hair coloring, spot laundry cleaning, skin and nail care, and polishing, as well as numerous others.

26 Claims, 6 Drawing Sheets

U.S. PATENT DOCUMENTS

| | | | |
|---|---|---|---|
| 5,100,252 A | | 3/1992 | Podolsky .................... 401/174 |
| 5,114,255 A | * | 5/1992 | Villarreal ..................... 401/45 |
| 5,174,475 A | * | 12/1992 | Day et al. ................ 222/144.5 |
| 5,186,559 A | * | 2/1993 | Fu ............................... 401/47 |
| 5,226,206 A | | 7/1993 | Davidovitz et al. .......... 15/22.1 |
| 5,276,932 A | | 1/1994 | Byrd ............................. 15/28 |
| 5,289,604 A | | 3/1994 | Kressner ..................... 15/22.1 |
| 5,309,590 A | | 5/1994 | Giuliani et al. .............. 15/22.1 |
| 5,353,460 A | | 10/1994 | Bauman ..................... 15/22.1 |
| 5,383,242 A | | 1/1995 | Bigler et al. ................ 15/22.1 |
| 5,403,105 A | * | 4/1995 | Jameson ...................... 401/45 |
| 5,476,384 A | | 12/1995 | Giuliani et al. ............. 433/216 |
| 5,504,959 A | | 4/1996 | Yukawa et al. ............... 15/22.1 |
| 5,630,527 A | * | 5/1997 | Beebe et al. .................... 222/1 |
| 5,765,722 A | * | 6/1998 | Beebe et al. .................... 222/1 |
| 5,842,487 A | | 12/1998 | Ledet ......................... 132/308 |
| 5,848,730 A | * | 12/1998 | Kawase et al. ................ 222/94 |
| 5,881,902 A | | 3/1999 | Seager et al. ................ 222/137 |
| 5,909,977 A | | 6/1999 | Kuo ........................... 401/146 |
| 5,943,723 A | | 8/1999 | Hilfinger et al. ............. 15/22.1 |
| 5,991,921 A | | 11/1999 | Saito ............................... 2/69 |
| 5,997,201 A | | 12/1999 | Bossert et al. ................ 401/75 |
| 6,056,463 A | * | 5/2000 | Nishio et al. ................. 401/47 |
| 6,089,407 A | * | 7/2000 | Gardos ....................... 222/137 |

* cited by examiner

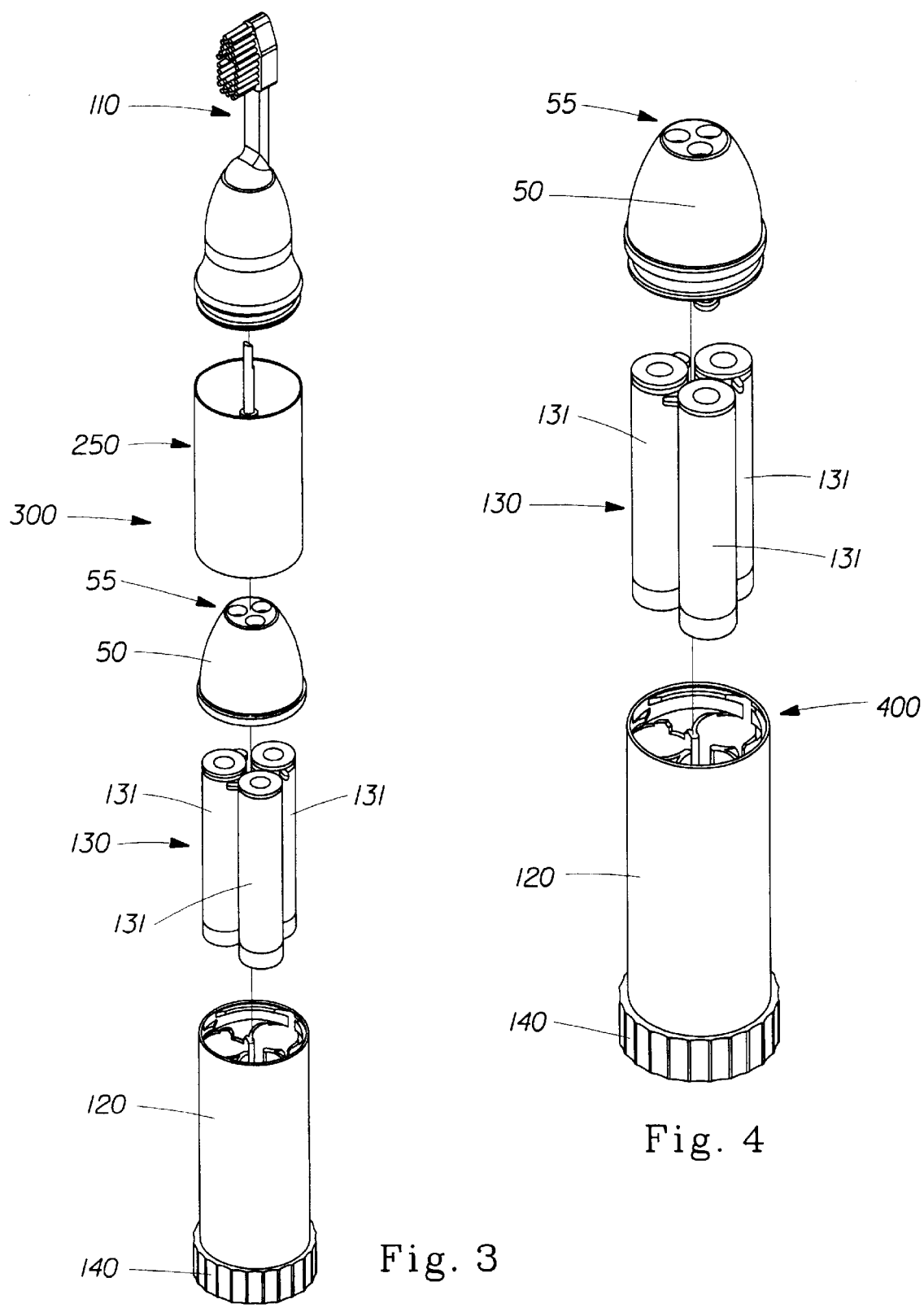

APPARATUS, METHOD AND PRODUCT FOR TREATING TEETH

BACKGROUND OF THE INVENTION

1. Field of the Invention

The present invention relates to apparatus, methods and products for dispensing a material. In another aspect, the present invention relates to apparatus, methods and products for providing a material to a surface. In even another aspect, the present invention relates to dental treatment devices, methods of treating teeth and oral tissue during brushing, and to products containing dental treatment materials. In still another aspect, the present invention relates to toothbrushes, methods of treating teeth and oral tissue during brushing, and to cartridges containing dental treatment materials. In yet another aspect, the present invention relates to toothbrushes for dispensing dental treatment materials, to methods of treating teeth by dispensing a treatment material from a toothbrush during brushing, and to cartridges containing dental treatment materials for use with dispensing toothbrushes. In even still another aspect, the present invention relates to apparatus, methods and products useful in nail, hair and/or skin care, jewelry making or cleaning, grout cleaning, auto detailing, painting, furniture painting/staining/refinishing, spot burnishing, spot laundry cleaning, and ceramics painting/finishing.

2. Description of the Related Art

Periodontal disease is primarily caused by complex aggregates of microorganisms, primarily bacteria, in the crevice regions between the teeth and the teeth and the gums. These aggregates are commonly referred to as dental plaque.

Outside of the dentist's office, brushing with conventional toothbrushes and flossing are currently the standard methods of removing, disrupting and dispersing dental plaque.

The oldest and most common type of toothbrush is the traditional manual toothbrush, having bristles upon which is applied, a dentifrice, such as a paste, gel or powder, to assist in tooth brushing. The toothbrush bristles are then manually manipulated against teeth and gums in an effort to remove, disrupt and disperse dental plaque.

U.S. Pat. No. 5,276,932, issued Jan. 11, 1994, to Byrd, discloses improvements to the traditional manual bristle toothbrush. The brush includes a slidable thumb actuated mechanism in the handle mechanically linked to rotary bristles in the head of the toothbrush. Longitudinal reciprocative motion of the thumb mechanism causes rotation of the rotary bristles.

In addition to manual toothbrushes, there are powered toothbrushes, which provide, some sort of manipulating motion to the bristles, for example rectilinear or rotational motion, to assist in brushing. Examples of powered toothbrushes include, U.S. Pat. Nos. 3,927,435; 5,226,206; 5,289,604; 5,353,460; 5,383,242; 5,476,384; 5,504,959; 5,309,590; and 5,943,723.

Whether using a manual or powered toothbrush, the problem with placing a dentifrice on the bristles, is the lack of accurate and repeatable amount of dentifrice. For example, the concentration of dentifrice on the bristles is at a maximum just after application of a dentifrice to the bristles, but prior to brushing. Commencement of brushing quickly results in a decrease of the concentration of dentifrice on the bristles, and a resulting reduction in the advantage provided by the dentifrice.

While it is possible to occasionally stop brushing, and reapply the dentifrice to the bristles, a more practical approach would be to provide the toothbrush with a reservoir from which the dentifrice is dispensed during brushing, either intermittently or continuously.

Such an idea is not new. For example, U.S. Pat. No. 730,040, issued Jun. 2, 1903 to McKinley et al., discloses a toothbrush having a receptacle for feeding a liquid dentifrice into the bristles of the brush; U.S. Pat. No. 3,217,720, issued Nov. 16, 1965 to Cyzer, discloses a toothbrush with a liquid dentifrice container; and U.S. Pat. No. 5,909,977, issued Jun. 8, 1999 to Kuo, discloses a dentifrice dispensing toothbrush utilizing a refillable cartridge for storing dentifrice material and a compressible elastic button for pumping dentifrice material to the brush head. Further development of this idea includes the use of hollow bristles through which the dentifrice flows as disclosed in U.S. Pat. No. 5,309,590, issued May 10, 1994 to Giuliani et al.

Recent developments in the fight against periodontal disease includes medications for inhibiting or killing bacteria responsible for periodontal disease, and the use of such medications has been promoted to the public for such a purpose. Such medications may be used in toothpaste, mouthwash, or solutions applied to the areas of interest. However, such medications are typically expensive when used on a daily basis, have been found to stain teeth in some cases with prolonged use, and in other cases, such as when they are in a mouthwash, are only marginally effective. Applying medication with brushing is convenient for the user and results in the treated area simultaneously undergoing cleaning and the application of medication. However, medication is typically not carefully applied in controlled amounts during brushing. There currently is no convenient way of assuring the application of only therapeutic amounts which require precision dosing and/or precision ratio control, so as to not cause tooth or oral tissue damage and/or prevent waste of the medication, while still being fully effective.

However, in spite of the above advancements, there still exists a need in the art for apparatus, methods and products for treating teeth.

There is another need in the art for apparatus, methods and products for treating teeth, which do not suffer from the disadvantages of the prior art apparatus, methods and products.

These and other needs in the art will become apparent to those of skill in the art upon review of this specification, including its drawings and claims.

SUMMARY OF THE INVENTION

It is an object of the present invention to provide for apparatus, methods and products for treating teeth and/or oral tissue.

It is another object of the present invention to provide for apparatus, methods and products for treating teeth, which do not suffer from the disadvantages of the prior art apparatus, methods and products.

These and other objects of the present invention will become apparent to those of skill in the art upon review of this specification, including its drawings and claims.

According to one embodiment of the present invention, there is provided a brushing system, which includes at least two material reservoirs, and further includes a tooth brush having bristles, wherein the bristles are in liquid communication with the two material reservoirs.

According to another embodiment of the present invention, there is provided a brushing system including at least one material reservoir, wherein the material reservoir comprises at least two materials, and wherein the materials are positioned to sequentially empty from the reservoir. The brushing system further includes a tooth brush having bristles, where the bristles are in liquid communication with the at least one material reservoir.

According to even another embodiment of the present invention, there is provided a method of brushing teeth with a brushing system, wherein the brushing system comprises at least two material reservoirs having dental treatment materials positioned within the reservoir, and a tooth brush having bristles, wherein the bristles are in liquid communication with at least two material reservoirs, the method first includes dispensing dental treatment materials from the reservoirs to the bristles. The method then includes contacting the bristles to teeth.

According to still another embodiment of the present invention, there is provided a method of brushing teeth with a brushing system, wherein the brushing system comprises a material reservoir having first and second dental treatment materials positioned within the reservoir, and a tooth brush having bristles, wherein the bristles are in liquid communication with the reservoir, the method first includes dispensing first dental treatment materials from the reservoir to the bristles. The method also includes applying the bristles to teeth. The method even also includes dispensing second dental treatment materials from the reservoir to the bristles. The method then includes applying the bristles to teeth.

According to yet another embodiment of the present invention, there is provided a reservoir system for use with a brush system, wherein the brush system comprises a tooth brush having bristles, and wherein the tooth brush defines a liquid communication passage through the tooth brush to the bristles, the reservoir system includes a body defining a reservoir having a dispensing passage for engaging the liquid communication passage.

These and other embodiments of the present invention will become apparent to those of skill in the art upon review of this specification, including its drawings and claims.

BRIEF DESCRIPTION OF THE DRAWINGS

FIG. 3 is an exploded view of brushing system 300, including drive 250, holder 120, and dispensing actuator 140.

FIG. 4 is an exploded view of brushing system 400, including holder 120, and dispensing actuator 140.

DETAILED DESCRIPTION OF THE INVENTION

The dispensing system of the present invention includes a cartridge assembly of one or more cartridges for storing dental treatment materials, which cartridges may be manually or motor driven to dispense the dental treatment materials, either directly onto the applicator of a tooth brush, or through passages in the tooth brush onto or through an applicator. The applicator may be any suitable device for applying dental treatment materials to teeth or to another device, including bristles, hollow dispensing tube (for application of the dental treatment materials directly to the teeth/gums or to another device such as a toothbrush), sponge, and/or nubs (a knobbed, roughened, or multicontoured surface for contacting teeth and/or gums). The dispensing system generally also includes a cartridge holder, and a dispensing actuator, as in a knob, button, or similar means.

Figure 1:
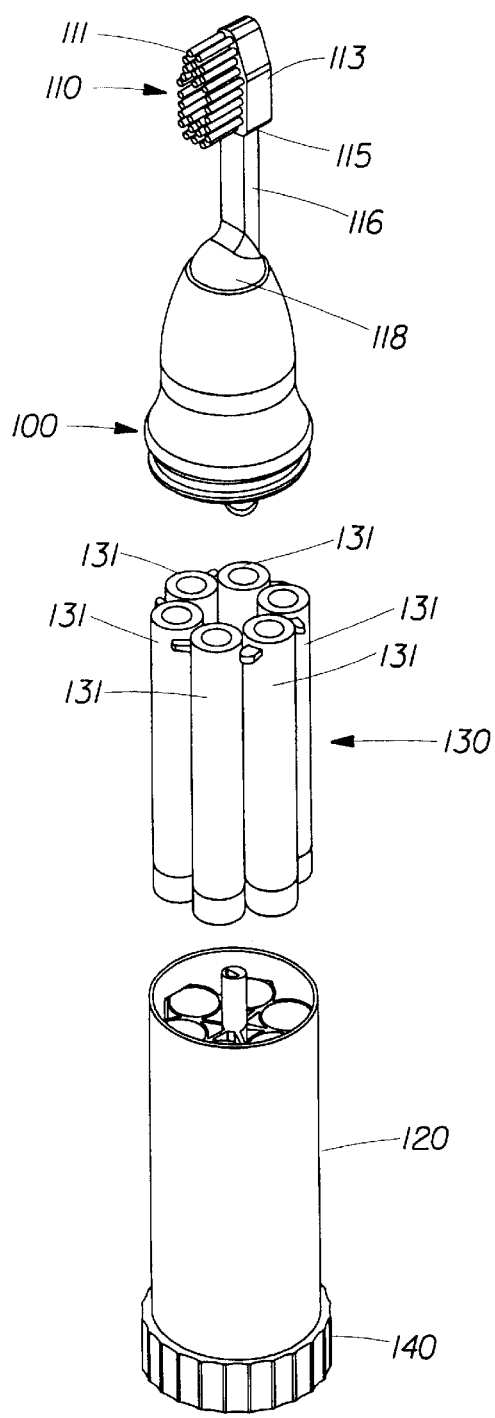
FIG. 1 is an exploded view of brushing apparatus 100 of the present invention, including tooth brush 110, holder 120, cartridge assembly 130, and dispensing actuator 140.

Referring first to FIG. 1, there is shown an exploded view of a manually powered brushing apparatus 100 of the present invention, including tooth brush 110, and dispensing system cartridge holder 120, cartridge assembly 130, and a dispensing actuator 140.

Cartridge assembly 130 includes a number of reservoirs shown as cartridges 131. One advantage of a multiple cartridge dispensing system of the present invention, is that materials that would be incompatible for storage together, may be stored in separate cartridges and then dispensed together for use at the point of use. Because the materials are mixed at the brush head as needed, there is better control over the amount of product mixed, resulting in minimal or no wasted mixed product to discharge or waste after use.

Tooth brush 110 includes bristles 111, brush head 113, duckbills 117, neck 115, body 116, and connector 118.

Any suitable reservoir or cartridge may be utilized in the present invention. It should be understood that the reservoir or cartridge utilized may be fully or partially internal to the dispensing system, or fully or partially external to the system, and may or may not be removable from the system. Additionally, the reservoir or cartridge utilized may be permanent to the system, or may be disposable, including a single use disposable reservoir. Non-limiting examples of suitable reservoirs include positive displacement type reservoirs which are generally rigid-walled such as a cartridge, and also include pump-evacuated type reservoirs which are generally soft-walled such as sachets, bladders, and blisters.

Figure 7:
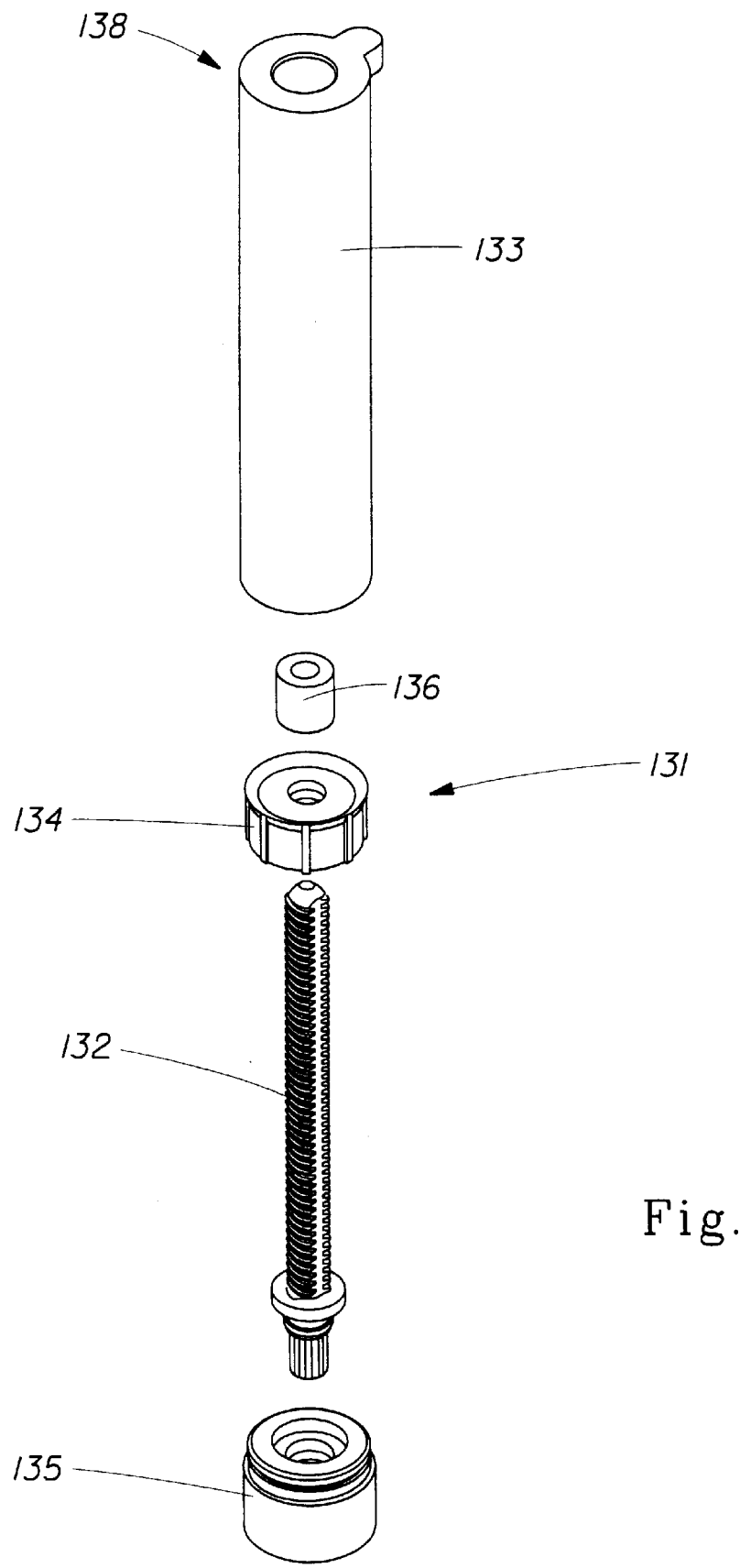
FIG. 7 is a view of cartridge 131 of FIG. 1, in which power is provided to bottom of screw 132 to drive piston 134 and seal 136 that in turn pushes material through cartridge housing 133 out opening 138.

As a non-limiting example, reference is made to FIG. 7, showing cartridge 131 of FIG. 1, with a piston 134 and seal 136 that pushes material through the cartridge housing 133. Power provided to gear 137 rotates screw 132 to drive piston 134. An optional cap, may be provided to seal cartridge 131 when not in use. Of course, for reservoirs having the screw type mechanism as shown in FIG. 7, it should be understood that the taper or pitch of the screws for each of the reservoirs, may be the same or different, to effect various ratios of material delivery.

Manual rotation of dispensing actuator 140 causes rotation of cartridge gear 137.

In the practice of the present invention, the cartridges may be adapted for dispensing equal or different amounts of material. For example, for a required mixture of materials A, B, and C, in a ratio of 1:1:1, the cartridges for materials A, B, and C will be adapted to dispense at a ratio of 1:1:1. As another example, for a required mixture of materials A, B, and C, in a ratio of 1:3:1, the cartridges for materials A, B, and C will be adapted to dispense at a ratio of 1:3:1.

The dispensing amount of any particular cartridge may be adjusted by any suitable means, non-limiting examples of which include varying the motor speed to the dispensing mechanism, and include changing the mechanical advantage of the dispensing mechanism (for example by substituting screws having various screw pitch or by utilizing different ratio gears for driving the screw). For other variations of cartridge designs, rate and amount of product can be controlled by means such as orifices, speed/timing relationships, pumps, etc.

The dispensing system of the present invention may be utilized for the delivery of very precise, controlled or efficacious amounts of treatment materials. This is very important when close tolerances are required in the ratios between the various treatment materials that make up a total treatment regimen. These required amounts may be delivered utilizing the screw and gear delivery system as described above, in which a known rotation of the screw will deliver a precise, controlled and repeatable amount of material.

One or more of the cartridges of the present invention may also be loaded with dental treatment material in a sequential fashion. For example, one particular cartridge may be loaded with materials A, B, C and then D, so that the cartridge will sequentially dispense material A, then material B, then material C and then material D. As a non-limiting example, a cartridge may be loaded to sequentially dispense a tooth cleaner, then a tooth polisher, then a fluoride agent, and finally a tooth sealant. Any suitable desired sequential loading of material may be utilized.

Sequential dispensing of materials may also be accomplished by sequentially dispensing from different cartridges or combinations of cartridges. As a non-limiting example only, for a system with cartridges A, B, C and D containing respectively, a rinse (A), a first component of tooth cleaner (B), a second component of tooth cleaner (C), and a fluoride agent (D), the desired dispensing may be from cartridge A (rinse), then simultaneously from cartridges B and C (first and second components of tooth cleaner), then from cartridge A again (rinse), and then from cartridge D (fluoride agent).

It should also be understood, that a number of repeatable sequences can also be dispensed from either one cartridge or a combination of cartridges. For example, N number of treatment regimens could be positioned in the material reservoir, with each regimen comprising material A and a material B. N is generally an integer of at least 1, preferably at least 2, more preferably at least 7, even more preferably at least 31, still more preferably at least 90, and yet more preferably at least 365. This series of N regimens is positioned to allow emptying of substantially all of the material A of the Nth regimen prior to application of the material B of the Nth regimen, and positioned to allow emptying of substantially all of the material B of the Nth regimen prior to application of the material of the next or (N+1)th regimen. Of course, the Nth (or last) regimen will empty after all of the N−1 (or second to last) regimen has substantially emptied. More specifically, the last material of the Nth (or last, or in the case of N=1, the only) regimen, will empty after all of the second to last material of the Nth (or last, or in the case of N=1, the only) regimen.

It should be understood that while the regimen above is illustrated as having materials A and B, and suitable number of materials may be utilized. As another non-limiting example, The system of claim 14 wherein each regimen further comprises three materials A, B, and C, positioned to allow emptying of substantially all of the first material A of the Nth regimen prior to application of the second material B and third material C of the Nth regimen, and to allow emptying of substantially all of the second material B of the Nth regimen prior to application of the third material C of the Nth regimen, and positioned to allow emptying of substantially all of the third material C of the Nth regimen prior to application of the first material A of the (N+1)th regimen.

As used herein, "substantially emptying" shall mean that at least about 25 weight percent, preferably at least about 50 weight percent, more preferably at least about 75 weight percent, even more preferably at least about 95 weight percent, still more preferably at least about 98 weight percent, and yet more preferably at least about 99 weight percent, of the one material will empty before the other starts emptying.

To accomplish dispensing from different cartridges or combinations of cartridges, a regulator or switch system able to allow selection of a cartridge or combination of cartridges may be utilized. For example, a rotational or other positioning system my be utilized to orient one or more of the desired cartridges to be in fluid communication with the dispenser, with the remaining cartridges out of fluid communication. As an alternate example, a system which positions the dispenser to be in fluid communication with one or more cartridges as desired may also be utilized. As another alternate example, a system which positions both the dispenser and the desired cartridges may also be utilized. Another suitable system includes one which utilizes a conduit, such as a tube or hose, between each of the reservoirs and the dispenser, with conduits selectively opened or closed by switches to deliver material as desired.

Whether dispensed from one cartridge or a combination of two or more cartridges, any suitable combination of sequential treatment regimen may be created from the list of dental treatment materials as provided below.

Another non-limiting example of a sequential treatment regimen includes high strength whitening followed by whitening maintenance treatment.

Even another non-limiting example of a sequential treatment regimen includes stanous fluoride followed by a stain removing treatment.

Still another non-limiting example of a sequential treatment regimen includes whitening agent and sealer to prevent staining.

Yet another non-limiting example of a sequential treatment regimen includes aggressive medication followed by a neutralizing agent.

Even still another non-limiting example of a sequential treatment regimen includes tooth cleaner followed by breath freshener/treatment.

Even yet another non-limiting example of a sequential treatment regimen includes tooth cleaner, tooth polisher, then sealant.

For consumer ease of use, it is envisioned that some brushing systems may be predisposed to dispense in a certain order. For example, for the sequential example just provided above, the brushing system would be available to dispense automatically from cartridge A, then from cartridges B and C, then from cartridge A, and finally from cartridge D.

With the advent of cheaper and smaller microprocessors, the brushing system could even contain a preprogrammed or programmable microprocessor to control the dispensing of material. The microprocessor would be connected to the mechanism which control cartridge selection and product dispensing. This control can include the selection of the desired cartridges or combinations of cartridges, the order of dispensing, as well as the amount dispensed from each cartridge.

Of course, to enhance dental care this microprocessor system could be programmed to provide alarms or messages to a small display screen to remind the user to dispense certain materials at certain times. For example, for two dental treatments one to be dispensed from cartridge A every 4 hours, the other to be dispensed from cartridge B every six hours, the brushing system could be programmed to so dispense, with reminders/alarms to the user to use the brush at the appropriate times.

It is even envisioned that a given pre-loaded multiple cartridge system may further include its own executable instructions on a medium (for example a small chip, disk, microprocessor, or Radio Frequency ID tag to activate proprietary program functions) that is loaded into the brushing system to dispense material from the cartridge system as desired.

Cartridge assembly 130 fits inside cartridge holder 120, with one or more of the cartridges 131 in liquid communication with stems 37. Of course, dispensing actuator 140 must be sufficiently accessible to all rotation of dispenser actuator 140.

In the practice of the present invention, it is envisioned that pre-loaded cartridges 131 may be available as single use disposable cartridges, multiple use disposable cartridges, or refillable cartridges, and that empty cartridges may be available for loading with suitable materials by the end user.

Figure 5:
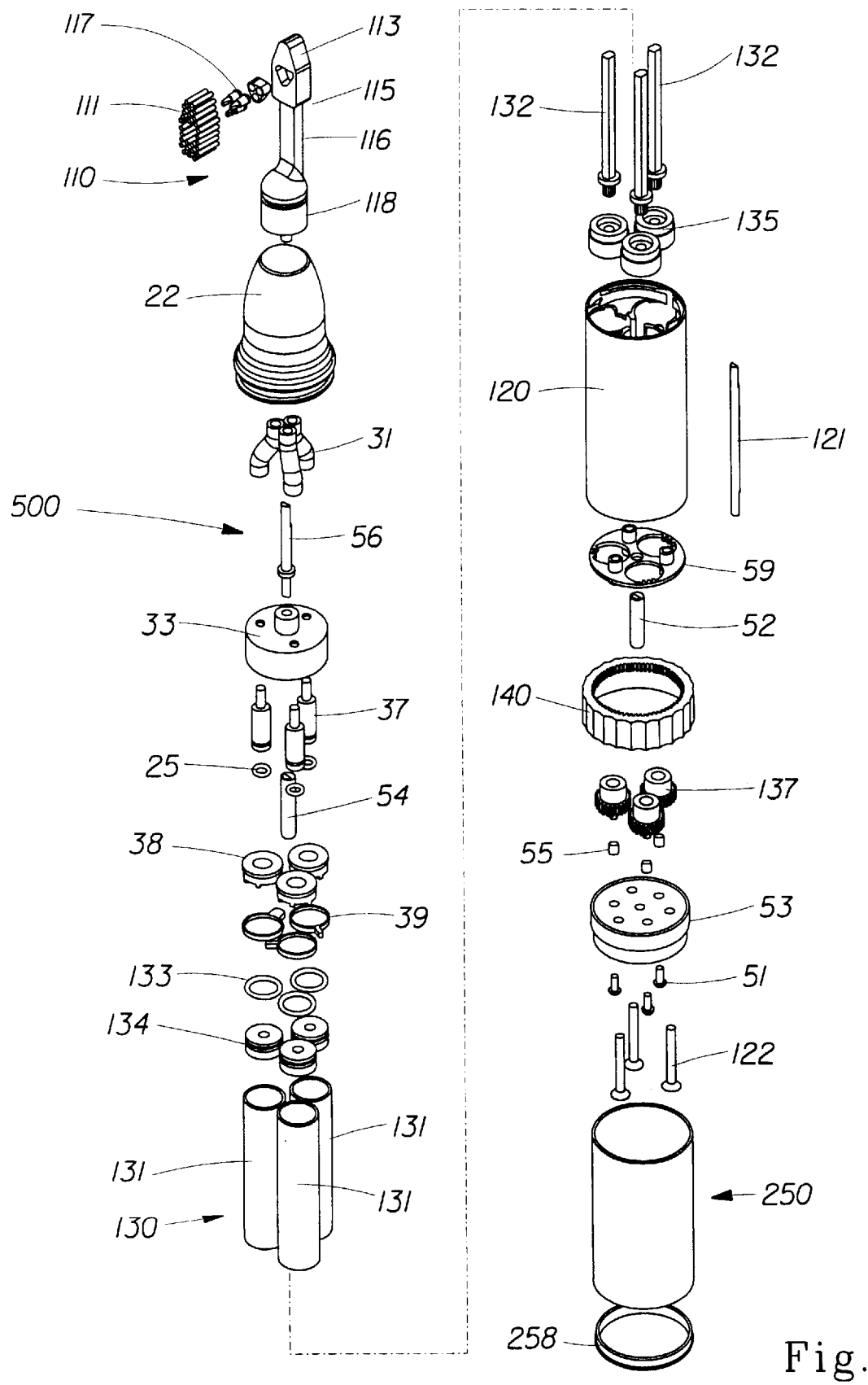
FIG. 5 is an exploded view of rigid cartridge brushing system 500, including tooth brush 110, cartridge assembly 130, holder 120, electric drive motor 250, and having tubes 131 that are rigid.

Referring now to FIG. 5, there is shown an exploded view of rigid cartridge brushing system 500, including tooth brush 110, cartridge assembly 130, holder 120, electric drive motor 250, and having cartridges 131 that are rigid. End cap 258 is positioned on the end of drive housing 250 and provides for convenient access to the inside of drive housing 250. Attached to drive housing 250, gear housing 53 is held in place by a number of retaining screws 122 which pass through interlock ring 59 and screw into housing 120. A number of gears 137 are positioned on top of gear housing 53 and held positioned by a number of springs 55 and screws 51. Dispensing actuator 140 fits around and engages gears 137. Positioned within holder 120 are one or more cartridge tubes 131, having end cap 135, piston 134 and a screw 132. Key 39 and fitment 38 serve to align cartridge tubes 131. Stems 37 are in liquid communication with cartridge tubes 131, and extend through manifold 33, and connect to and are in liquid communication with flexible delivery tubes 31 connected to and in liquid communication with connector 118 and duckbills 117. Tooth brush 110 passes through transition 22 and connects to drive shaft 56. Toothbrush 110 consists of duckbills 117, brush head 113, bristles 11, neck 115, body 116, and connector 118. As used herein, a "duckbill" is generally described as a resiliant flow regulator or check valve that includes a pair of lips arranged in a converging relationship to define an open end and a normally closed end. At the normally closed end the lips are disposed adjacent to each other to define a normally closed slit and define inner and outer surfaces for the lips. As fluid passes through the lips increased pressure will cause a larger opening, increasing the flow rate. With no pressure acting on the lips, closure prevents any material from entering opposite the desired material flow direction. Drive shaft 56 is connected to coupling 54, which is in turn connected to coupling 52 by drive shaft 121.

Figure 6:
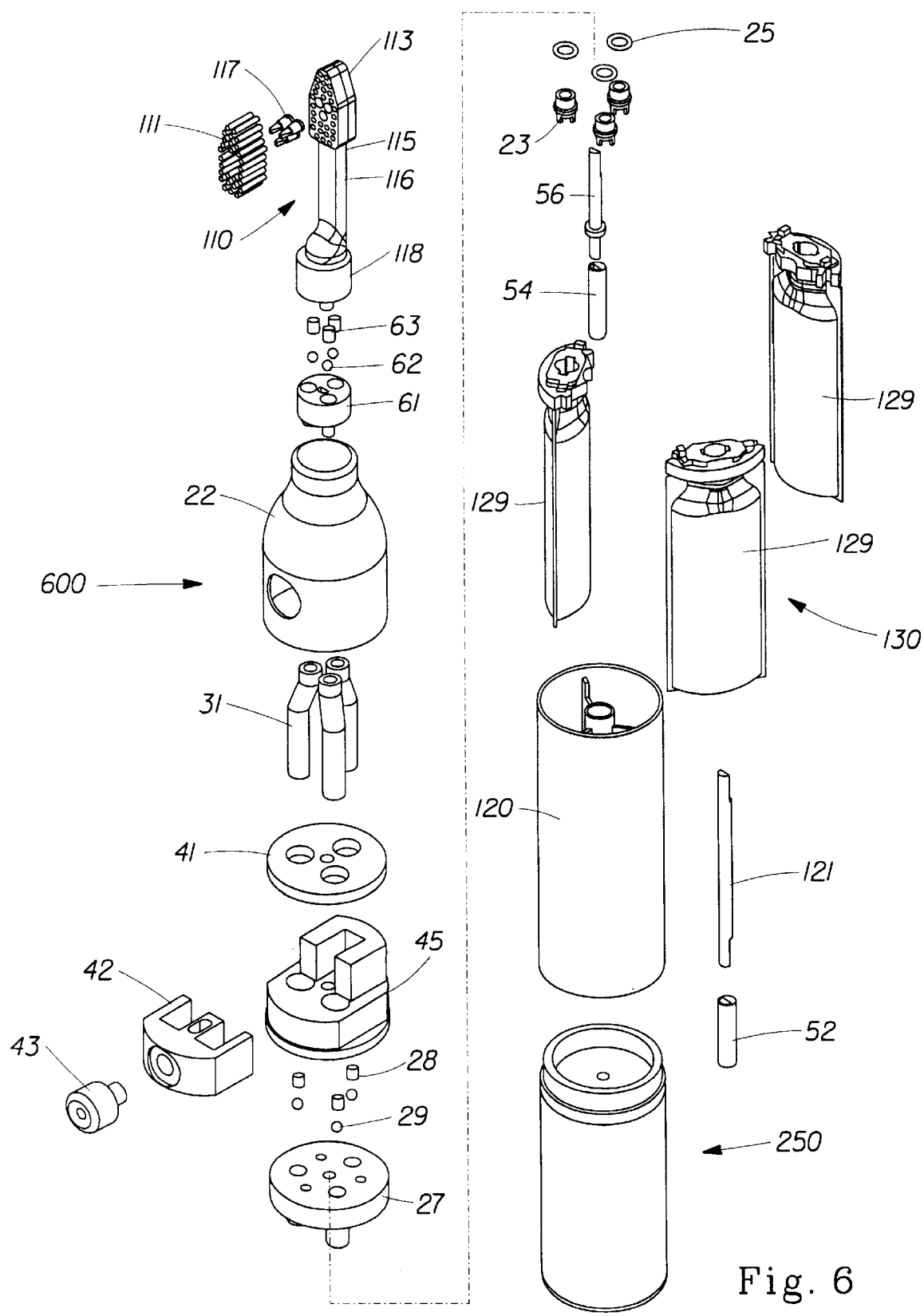
FIG. 6 is an exploded view of flexible sachet brushing system 600, including tooth brush 110, cartridge assembly 130, housing 120, electric motor drive motor 250, and having cartridges 129 that are flexible.

FIG. 6 is an exploded view of flexible sachet brushing system 600, including tooth brush 110, cartridge assembly 130, housing 120, electric motor drive motor 250, and having sachet 129 that are flexible. Inside holder 120 are positioned one or more sachets 129. The delivery mechanism includes stems 23 in liquid communication with sachets 129 and flexible tubes 31, o-rings 25, manifold 27, steel balls 29, springs 28. Anvil 45, pump actuator 42, button 43, and retainer disk 41 make up the remainder of the fluid delivery system. Included in the connection between housing 120 and tooth brush 110 are cap 61, steel balls 62 and springs 63. Tooth brush 110 passes through transition 22 and connects to drive shaft 56 and includes duckbills 117, bristles 111, brush head 113, neck 115, body 116, and connector 118.

In the practice of the present invention, dental treatment materials may be selected from the group consisting of anti-bacterial agents, bleaching agents, breath conditioning agents, buffers, carriers, cleaners, coatings, colorants or dyes (to impart color to the material), coloring or dying agents (for coloring or dying the tooth), conditioners, emulsifiers, foaming agents, fillers, flavors, flow agents, fluorides, gelling agents, inert agents, medicines, oxidizing agents, polish, preservatives, sealants, scrubbing agents, stain removers, surfactants, tartar control agents, thickening agents, viscosity agents, washes, whiteners, and the like. These dental treatment materials may be in emulsion, gel, granule, liquid, paste, powder, or slurry form.

In some embodiments of the present invention, it is to be understood that certain dental treatment materials or combination of dental treatment materials perform better in concentrated form, without the addition of solvents, diluents, thickening agents, viscosity agents, buffers, carriers, emulsifiers, surfactants, and the like. Thus, for those embodiments, it is preferred that those dental treatment materials or combination of materials be provided without the presence of such solvents, diluents, thickening agents, viscosity agents, buffers, carriers, emulsifiers, surfactants, and the like since the treatment materials are delivered from within the bristles.

Non-limiting examples of suitable fluoride treatments include stannous fluoride, sodium fluoride, and sodium monofluorophosphate. Current dental treatment materials contain solvents, dilutants, thickening agents, and the like to provide support for the treatment material while dispensed on top of toothbrush bristles. The preferred fluoride treatment is sodium fluoride.

The concentration of the various dental treatment materials will be chosen according to health and treatment standards as are known in the dental treatment art.

The dental treatment materials of the present invention will have a viscosity suitable for use in tooth treatment applications and methods.

As used herein, the "viscosity" shall refer to "dynamic viscosity" and is defined as the ratio of the shearing stress to the rate of deformation.

When measured at a shear rate of 1 seconds$^{-1}$, the viscosity will have a range with the lower end of the range generally about 0.0025 poise, preferably about 0.1 poise, and more preferably about 75 poise, with the upper end of the range being selected independently of the lower end of the range and generally about 10,000 poise, preferably about 5,000 poise, and more preferably about 1,000 poise. Non-limiting examples of suitable viscosity ranges when measured at a shear rate of 1 seconds$^{-1}$ includes, about 0.0025 poise to about 10,000 poise, about 0.1 poise to about 5,000 poise, about 75 poise to about 1000 poise, and about 0.1 poise to about 10,000 poise.

When measured at a shear rate of 100 seconds$^{-1}$, the viscosity will have a range with the lower end of the range generally about 0.0025 poise, preferably about 0.05 poise, and more preferably about 7.5 poise, with the upper end of the range being selected independently of the lower end of the range and generally about 1,000 poise, preferably about 100 poise, and more preferably about 75 poise. Non-limiting examples of suitable viscosity ranges when measured at a shear rate of 100 seconds$^{-1}$ includes, about 0.0025 poise to about 1,000 poise, about 0.05 poise to about 100 poise, about 7.5 poise to about 75 poise, and about 0.05 poise to about 1,000 poise.

When measured at a shear rate of 10,000 seconds$^{-1}$, the viscosity will have a range with the lower end of the range generally about 0.0025 poise, preferably about 0.05 poise, and more preferably about 5 poise, with the upper end of the range being selected independently of the lower end of the range and generally about 500 poise, preferably about 50 poise. Non-limiting examples of suitable viscosity ranges when measured at a shear rate of 10,000 seconds$^{-1}$ includes, about 0.0025 poise to about 500 poise, about 0.05 poise to about 50 poise, about 5 poise to about 50 poise, and about 0.05 poise to about 500 poise.

Continuing with FIG. 6 toothbrush 110 includes body 116, neck 115, bristle head 113, duckbills 117, bristles 111, and engaging connector 118. While not shown, toothbrush 110 includes one or more passages extending from engaging connector 118 to duckbills 117. In assembly, flexible delivery tubes 31 and 121 and cap 61 engage to provide liquid communication between sachets 129 and bristles 111.

In operation of embodiment 100, cartridge assembly 130 of cartridges 131 with suitable dental treatment materials are positioned in holder 120, with tooth brush 110 affixed to drive shaft 56. Dispensing actuator 140 engages cartridge gear 137. Rotation of dispensing actuator 140 provides rotational energy to dispense dental treatment material through brush 110 and duckbills 117 then to bristles 111.

Figure 2:
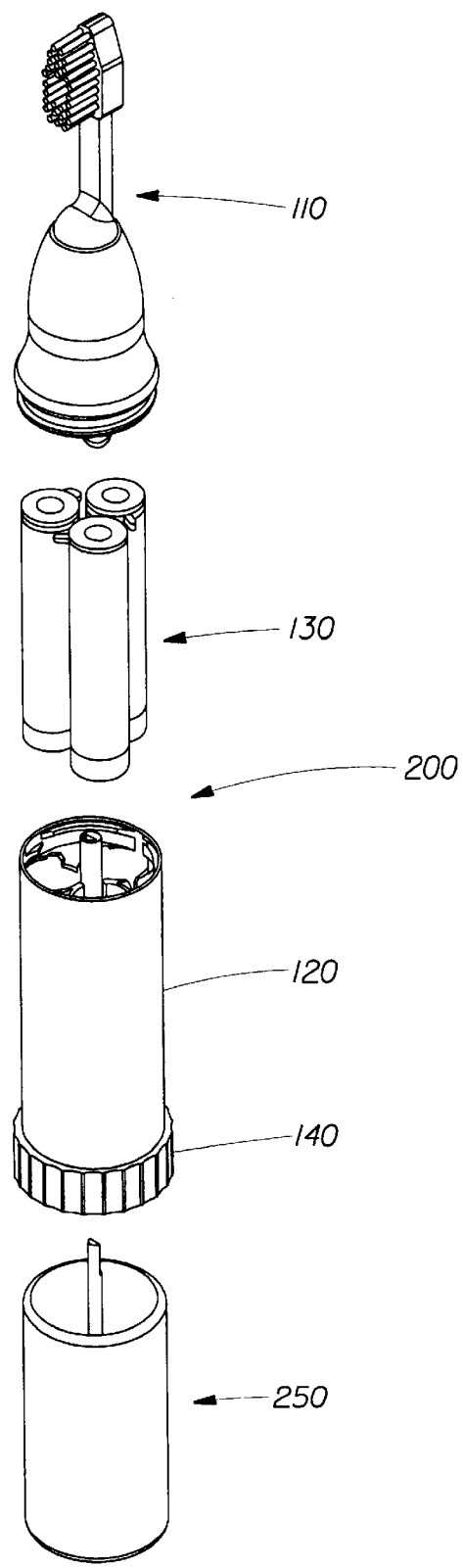
FIG. 2 is a view of an electric motor powered brushing apparatus 200 of the present invention, including tooth brush 110, and dispensing system cartridge holder 120, electric drive motor 250.

Referring now to FIG. 2, there is provided an electric motor powered brushing apparatus 200, of the present invention, including tooth brush 110, and dispensing system cartridge holder 120, electric drive motor 250. Cartridge assembly 130 resides in holder 120. Operation of brushing apparatus 200 is similar to that of brushing apparatus 100 except that an electric motor drive 250 has replaced the manual method of brushing.

Referring now to FIGS. 3 and 4, there are shown brushing systems 300 and 400, respectively, with brushing system 300 including drive 250, holder 120, and dispensing actuator 140, and brushing system 400 includes holder 120, and dispensing actuator 140. Both of these brushing systems 300 and 400 include dispensing cap 50 having a dispensing tip 55 in liquid communication with cartridges 131 residing in holder 120 for dispensing the dental treatment material directly onto the tooth brush bristles. For both of these embodiments 300 and 400, cartridge assembly 130 resides in holder 120. In operation, these embodiments are powered sufficiently to cause dental treatment materials to dispense from dispensing tip 55 for application to tooth brush bristles.

While embodiments of the figures are configured to provide simultaneous dispensing of materials from all of the cartridges, it should be understood that the brushing systems of the present invention may include regulators to allow for sequential dispensing of material from different cartridges or combinations of cartridges.

The tooth brushing system of the present invention finds utility mainly for use in the care of human teeth, although utility may also be found in animal husbandry, pet care, and veterinary applications.

Figure 8:
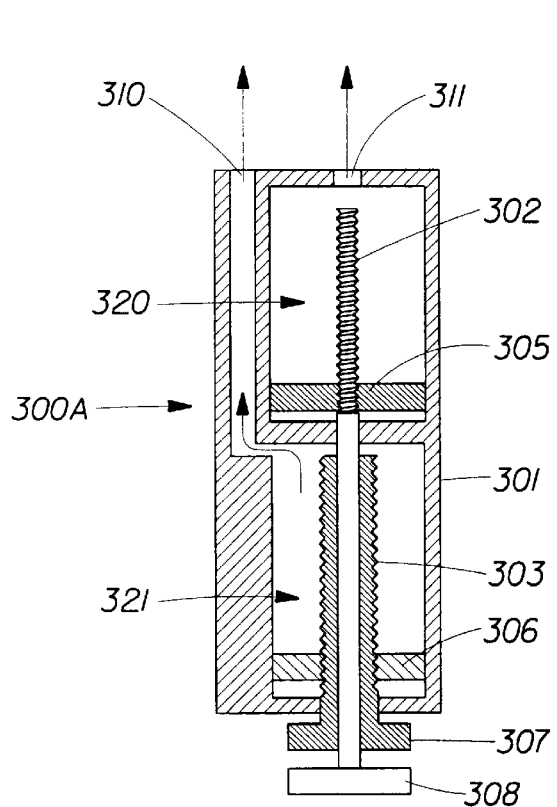
FIG. 8 is a side view of a two chamber cartridge and a concept which can be used to dispense 2 or more products from a 2 or more chambered cartridge.

Referring now to FIG. 8, there is shown two chamber cartridge 300A, a concept which can be used to dispense 2 or more products from a 2 or more chambered cartridge. The multiple products can be dispense simultaneously or individually. As shown, within housing 301 are 2 chambers, upper fluid chamber 320, and lower fluid chamber 321, but one can easily see that more than 2 can be utilized. Each chamber has a separate piston, upper piston 305 and lower piston 306, which are threaded respectively through upper drive screw 302 and lower drive screw 303. Upper piston 305 in top chamber 320 is threaded through screw 302 of a smaller diameter than piston 306 in the bottom chamber. Screw 302 for top chamber piston 305 is positioned inside of screw 303 for bottom chamber piston 306. Each chamber 320 and 321 is respectively in fluid communication with separate exit channels 311 and 310. Rotation of upper piston screw 302 and lower piston screw 303, with respectively, drive gear 308 and drive gear 307, causes the products contained in the respective chambers 320 or 321, to be forced out through the respective exit channels 311 or 310. Rotation of the two screws 302 and 303 can be accomplished simultaneously, to get both products at the same time, or individually to get one product at a time. One can also envision any number of different drive mechanisms and gearing configurations which could allow product to be dispensed in different sequences and ratios which could be selected by the person using the device.

Figure 9:
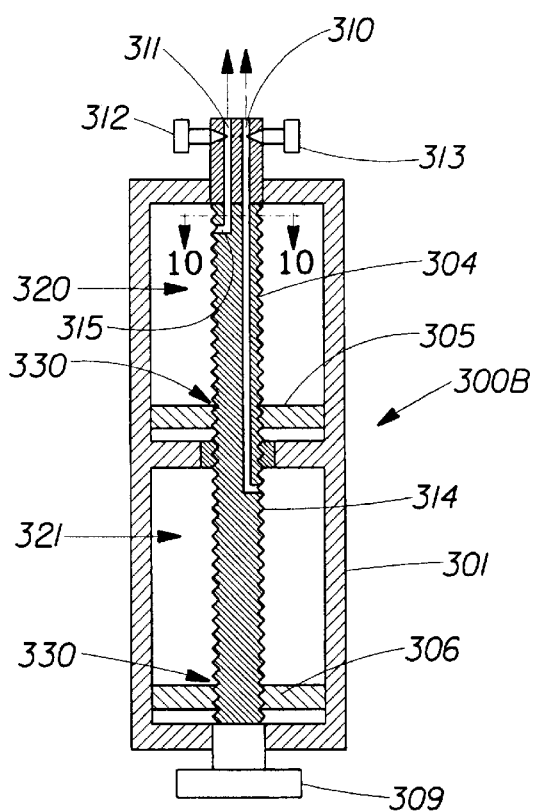
FIGS. 9 and 10 show side and screw cross section view, respectively, of another two chamber cartridge and a concept which can be used to dispense 2 or more products from a 2 or more chambered cartridge.
Figure 10:
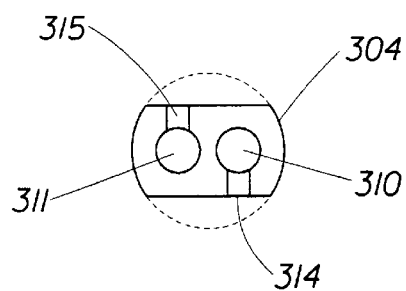

Referring now to FIGS. 9 and 10, there respectively shown side view and screen cross section view of two chamber cartridge 300B, which can be used to dispense 2 or more products from a 2 or more chambered cartridge. The multiple products can be dispense simultaneously or individually from upper fluid chamber 320 through fluid discharge 311, and/or from lower fluid chamber 321 through fluid discharge 310. As shown, housing 301 has 2 chambers, but one can easily see that more than 2 can be utilized. In operation, rotation of central screw 304 is accomplished by rotation of knob, gear, or other means 309 attached to screw 304 at the bottom of housing 301 as shown, or in some other location/position so as to drive rotation of the screw. Central drive screw 304 has two flow channels 310 and 311 through the center of it. Flow channel 311 is in fluid communication with the top chamber 320 and the other channel 310 is in fluid communication with bottom chamber 321. Rotation of screw 304 will drive upper piston 305 and lower piston 306 upward, forcing the product through into fluid inlet channels 315 and 314, respectively, and subsequently out through channels 311 and 310, respectively. Upper chamber valve 312 and lower chamber valve 313 can be used to shut off flow through channels 311 and 310, respectively. Also shown is piston to screw overrunning interface 330. The piston in the chamber which is in fluid communication with the valve which is shut off is designed to slide down the threads of the screw when internal pressure in the chamber reaches a higher level than normal due too the flow passage being shut off. In this way, one can shut off one channel or the other to get only one product at a time if desired. Furthermore the hollow screw could be part of the brush head and stem, or a dispensing nozzle, and therefore to dispense product up through a brush head or dispensing head, a person could just rotate the cartridge body or housing while holding the brush head or dispensing head stationary, or visa versa.

While the dispensing system of the present invention has been illustrated mainly by reference to in dental care, it should be understood that the dispensing system finds utility in a wide variety of arts. The dispensing system my be used alone to dispense a wide variety of materials, or may be used in combination with a wide variety of tools or instruments. As a non-limiting example, the dispensing system may be utilized in nail, hair and/or skin care (for humans or animals) to dispense, either directly or through a brush or other applicator, conditioners, coloring, creams, cleanser, emollients, lotions, medicines, polish, softeners, and/or any other nail, hair or skin treatment material. As other non-limiting examples, the dispensing system may be utilized in jewelry making or cleaning, grout cleaning, auto detailing, painting, furniture painting/staining/refinishing, spot burnishing, spot laundry cleaning, and ceramics painting/finishing. As even another non-limiting example, the dispenser system of the present invention finds utility in hair coloring with a wide variety of manual, powered, sonic, or ultrasonic applicator heads.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

All patents and articles cited herein, are hereby incorporated by reference.

We claim:

1. A tooth brushing system comprising:
   (a) a body;
   (b) a first material reservoir for supplying a first material;
   (c) a second material reservoir for supplying a second material;
   (d) an applicator supported by the body; and,
   (e) a switch;
   wherein the first and second material reservoirs are in continuous liquid communication with the applicator;
   wherein the first and second reservoirs are supported by the body;
   wherein the switch is positionable in a first position or a second position; and,
   wherein the first position engages the applicator in liquid communication with the first material reservoir and the second position engages the applicator in liquid communication with the second material reservoir.

2. The system of claim 1, wherein at least a portion of at least one of the first or second reservoirs are removably contained within said body.

3. The system of claim 2, wherein at least one of the first or second reservoirs comprises a positive displacement.

4. The system of claim 1, further comprising:
   (e) a first dental treatment material positioned in the first reservoir; and
   (f) a second dental treatment material positioned in the second reservoir;
   wherein the first dental treatment material is different from the second dental treatment material, and wherein the first and second dental treatment materials each comprise at least one selected from the group consisting of anti-bacterial agents, bleaching agents, breath conditioning agents, buffers, carriers, cleaners, coatings, tooth colorants or dyes, coloring or dying agents, conditioners, emulsifiers, foaming agents, fillers, flavors, flow agents, fluorides, gelling agents, inert agents, medicines, oxidizing- agents, polish, preservatives, sealants, scrubbing agents, stain removers, tartar control agents, viscosity agents, washes, and whiteners.

5. The system of claims 4, wherein said first material is provided without an additional thickening agent.

6. The system of claim 5, wherein the viscosity of the first materials, when measured at a shear rate of about 1 seconds$^{-1}$ is in the range of about 0.1 poise to about 5,000 poise.

7. The system of claim 5, wherein said second material is provided without an additional thickening agent.

8. The system of claim 7, wherein the viscosity of the first and second materials, when measured at a shear rate of about 100 seconds$^{-1}$, is in the range of about 0.05 poise to about 100 poise.

9. The system of claim 4, wherein the first material comprises fluoride, and the second material comprises at least one selected from gingivitis treatments, whitening agents, breath treatments, and combinations thereof.

10. The system of claim 1, further comprising:
    (e) a third material reservoir for supplying a third material, wherein the third reservoir is in liquid communication with applicator, and wherein the third reservoir is supported by the body; and
    (f) a third material positioned in the third reservoir, wherein the third material comprises at least one selected from the group consisting of whitening agents, advanced cleaning agents, baking soda, peroxide, tartar control, and combinations thereof.

11. The system of claim 10, further comprising:
    (g) a fourth material reservoir for supplying a fourth material, wherein the third reservoir is in liquid communication with applicator, and wherein the third reservoir is supported by the body; and
    (h) a fourth material positioned in the fourth reservoir, wherein the fourth material comprises at least one selected from the group consisting of whitening agents, advanced cleaning agents, baking soda, peroxide, tartar control, and combinations thereof.

12. A toothbrush comprising:
    (a) a body;
    (b) at least one material reservoir supported by the body, wherein the at least one material reservoir comprises at least one treatment regimen of at least two materials disposed therein, and wherein the at least two materials are positioned to sequentially dispense from the reservoir;
    (c) an applicator supported by the body, and in continuous liquid communication with the at least one material reservoir; and, wherein a first material of the at least two materials comprises a whitening agent and a second material of the at least two materials comprises a polisher.

13. The system of claim 12, further comprising:
   (d) N number of treatment regimens positioned in the material reservoir, wherein each regimen is positioned to allow dispensing of substantially all of the first material of the Nth regimen prior to application of the second material of the Nth regimen, and positioned to allow dispensing of substantially all of the second material of the (N−1)th regimen prior to application of the first material of the Nth regimen, and wherein N is an integer of at least 1.

14. The system of claim 13 wherein each regimen further comprises a third material, wherein each regimen is positioned to allow dispensing of substantially all of the first material of the (N−1)th regimen prior to application of the second and third materials of the Nth regimen, and to allow dispensing of substantially all of the second material of the (N−11)th regimen prior to application of the third material of the (N−1)th regimen, and positioned to allow dispensing of substantially all of the third material of the Nth regimen prior to application of the first material of the Nth regimen, and wherein N is an integer of at least 1.

15. The system of claim 13, wherein N is 1.

16. The toothbrush of claim 12 wherein the at least one treatment regimen of at least two materials comprises a first material and a second material wherein the first material is a cleaner and the second material is a breath conditioning agent.

17. The toothbrush of claim 12 wherein the at least one treatment regimen of at least two materials comprises a first material, a second material, and a third material, and wherein the first material is a cleaner, the second material is a medicine, and the third material is a breath freshening agent.

18. A method of brushing teeth with a brushing system, wherein the brushing system comprises a body, first and second material reservoirs supported by the body, an applicator supported by the body, wherein the applicator is in continuous liquid communication with the first reservoir and the second reservoir, and wherein the first material reservoir contains a first dental treatment material, and wherein the second material reservoir contains a second dental treatment material, and a switch to selectively dispense the first dental treatment material and the second dental treatment material, the method comprising the steps of:
   (a) engaging the switch to dispense the first dental treatment from the first reservoir to the applicator;
   (b) dispensing the first dental treatment material from the first reservoir to the applicator;
   (c) contacting the first dental treatment material to teeth;
   (d) engaging the switch to dispense the second dental treatment from the second reservoir to the applicator;
   (e) dispensing the second dental treatment material from the second reservoir to the applicator; and,
   (f) contacting the second dental treatment material to the teeth.

19. The method of claim 18 further comprising:
   prior to step (a), inserting said first and second reservoirs into said body.

20. A brushing system comprising:
   (a) a body;
   (b) an applicator supported by the body;
   (c) at least one insertably removable material reservoir supported by the body and having at least one material disposed therein;
   wherein said insertably removable material reservoir is in continuous liquid communication with sad applicator;
   (d) a screw and gear delivery system;
   wherein said screw and gear delivery system dispenses the at least one material from the insertably removable material reservoir to the applicator; and,
   wherein the delivery system is controlled by a microprocessor.

21. The brushing system of claim 20, wherein the brushing system comprises at least two insertably removeable material reservoirs.

22. The brushing system claim 20, wherein the microprocessor is programmable.

23. The tooth brushing system of claim 22, wherein said delivery system is adapted to dispense different amounts of the at least one material from each of the at least two insertably removeable material reservoirs.

24. A tooth brushing system comprising:
   (a) a body;
   (b) an applicator supported by the body;
   (c) at least two reservoirs capable of simultaneous dispensing;
   (d) at least two different materials disposed within the at least two reservoirs;
   wherein the at least two reservoirs are insertably removable within said body; and,
   wherein said at least two different materials are dispensed sequentially from said at least two reservoirs to said applicator.

25. The tooth brushing system of claim 24 wherein said at least two different materials are dispensed from said at least two reservoirs at a ratio not equal to 1.

26. A tooth brushing system comprising:
   (a) a body;
   (b) a plurality of material reservoirs;
   (c) an applicator supported by the body; and,
   (e) a switch;
   wherein each of the plurality of material reservoirs are in simultaneous liquid communication with the applicator;
   wherein the plurality of material reservoirs are supported by the body;
   wherein the switch is positionable in a first position or a second position; and,
   wherein the first position engages the applicator in liquid communication with a first material reservoir of said plurality of material reservoirs and the second position engages the applicator in liquid communication with a second material reservoir of said plurality of material reservoirs.

* * * * *

UNITED STATES PATENT AND TRADEMARK OFFICE
CERTIFICATE OF CORRECTION

PATENT NO. : 6,648,641 B1
DATED : November 18, 2003
INVENTOR(S) : Louis J. Viltro et al.

It is certified that error appears in the above-identified patent and that said Letters Patent is hereby corrected as shown below:

Column 13,
Line 20, delete "(N-11)" and insert -- (N-1) --.

Signed and Sealed this

Fifteenth Day of June, 2004

JON W. DUDAS
*Acting Director of the United States Patent and Trademark Office*